United States Patent [19]

DiPasquale

[11] Patent Number: 5,444,047
[45] Date of Patent: Aug. 22, 1995

[54] TREATMENT OF ARTHRITIC AND POST-SURGICAL ORTHOPEDIC CONDITIONS WITH INSULIN-LIKE GROWTH FACTOR-I

[76] Inventor: Gene DiPasquale, 75D Winthrop Rd., Jamesburg, N.J. 08831

[21] Appl. No.: 261,849

[22] Filed: Jun. 16, 1994

[51] Int. Cl.6 .................... A61K 38/00; A61K 38/17; C12N 15/63
[52] U.S. Cl. ......................... 514/12; 514/21
[58] Field of Search .................. 514/12, 21

[56] References Cited

U.S. PATENT DOCUMENTS

| | | | |
|---|---|---|---|
| 4,983,581 | 1/1991 | Antoniades et al. | 514/12 |
| 5,019,559 | 5/1991 | Antoniades et al. | 514/21 |
| 5,093,317 | 3/1991 | Lewis et al. | 514/12 |
| 5,126,324 | 6/1992 | Clark et al. | 514/12 |
| 5,128,320 | 7/1992 | Hahn et al. | 514/12 |
| 5,298,422 | 3/1994 | Schwartz et al. | 435/320.1 |

*Primary Examiner*—Jill Warden
*Assistant Examiner*—Lynn Touzeau
*Attorney, Agent, or Firm*—Frank S. Chow

[57] ABSTRACT

A method is disclosed which comprises a method for reducing atrophy in at least one striated skeletal muscle of an individual, comprising administering a therapeutically effective amount of Insulin-like Growth Factor-I (IGF-I) to said individual.

6 Claims, No Drawings

TREATMENT OF ARTHRITIC AND POST-SURGICAL ORTHOPEDIC CONDITIONS WITH INSULIN-LIKE GROWTH FACTOR-I

BACKGROUND OF THE INVENTION

Physical therapy, with specific exercises, has typically been recommended to maintain the mass of skeletal muscles, particularly those associated with injured or diseased joints. Increasing muscle mass can strengthen the muscular support structure for the joint and reduce impact loading on the joint, as well as reducing pain associated with use of the joint, such as occurs with arthritis.

However, as the arthritic process progresses or during periods of joint immobilization, such as following orthopedic surgery, skeletal muscle atrophy can occur in an affected limb. This atrophy weakens the skeletal muscle and can reduce the stability of, or destabilize, its associated joint, thereby resulting in damage to the joint and/or a lengthened recovery period.

Therefore, a need exists for a method of reducing skeletal muscle atrophy resulting from progressive disease, injury or joint immobilization.

SUMMARY OF THE INVENTION

The present invention relates to a method for reducing atrophy in at least one striated skeletal muscle of an individual, comprising of administering a therapeutically effective amount of Insulin-like Growth Factor-I (IGF-I) to said individual.

This invention has the advantage of maintaining or improving joint stability, by enhancing the mass of the associated skeletal muscle, during periods when said muscle is subject to atrophy.

DETAILED DESCRIPTION OF THE INVENTION

Muscle atrophy, as defined herein, is the loss of muscle mass, or strength, resulting from the reduced use or disuse of the muscle. Reduced use, or disuse, of an individual;'s skeletal muscle can occur due to cases which reduce the capacity of an associated diarthroses joint to move and/or to do work, wherein the skeletal muscle is utilized to move or support said joint, or which results in reducing the mobility of the individual. To do work means to move a weight a distance, for example walking or running, or to be under a strain, such as occurs in lifting a heavy load.

Reducing atrophy, as defined herein, means limiting the loss of muscle mass from atrophy and/or to increase gain in muscle mass after atrophy or in atrophy-susceptible conditions.

An individual, as described herein, is a human or another mammal, wherein said individual is hormonally about normal.

In one embodiment of the method of this invention, an individual has at last one skeletal muscle, which is susceptible to atrophy, or has atrophy, due to the lack of use of said skeletal muscle. A lack of use of a skeletal muscle can result from numerous cases, such as from injury or disease and also due to a limitation upon the mobility of the individual, such as being bedridden, at least partially paralyzed, or comatose. In this method, a therapeutically effective amount of Insulin-like Growth Factor-I (IGF-I) is administered to the individual to reduce atrophy of at least one skeletal muscle having reduced use.

In another embodiment, at least one diarthroses joint, for example ankle, knee, hip, should, elbow, or neck, or an individual has a reduced capacity due to a disease of said joint. The capacity of a joint is the ability of a joint to fully move and to do work. Diseases which can directly reduce the capacity of a joint to move or do work include, for instance, osteoarthritis, rheumatoid arthritis, bursitis, gout, rheumatic fever, tuberculosis, gonorrhea and the like. A skeletal muscle associated with said disease joint is susceptible to atrophy when the use of the joint is reduced or malalignment and altered biomechanics. In this method, a therapeutically effective amount of IGF-I is administered to the individual to reduce atrophy of at least one skeletal muscle, wherein the use of said skeletal muscle is reduced due to a diseased joint.

In yet another embodiment, an individual has at least one diarthroses joint having a reduced capacity resulting from a trauma. A trauma can result in reduced capacity of a joint, wherein there is trauma to said joint, to a skeletal muscle associated with said joint, or to another skeletal muscle, bone, joint or tendon, wherein said trauma affects the use of said joint and/or said skeletal muscle, such as through pain. A skeletal muscle associated with said reduced capacity joint is susceptible to atrophy when the use of the joint is reduced or biomechanical alteration. In this method, a therapeutically effective amount of IGF-I is administered to the individual to reduce atrophy of at least one skeletal muscle, wherein the use of said skeletal muscle is reduced due to a trauma.

In yet another embodiment of the method of this invention, at least one diarthroses joint of an individual has a reduced capacity due to a repair of a bone, joint, muscle and/or tendon ligament. A repair, as defined herein includes, for instance, surgical repair, the setting of fractures, and/or at least a partial immobilization of said joint. Immobilization of said joint, for example, can result from casting or splinting said joint. A skeletal muscle associated with said reduced capacity joint is susceptible to atrophy when the use of the joint is reduced. In this method, a therapeutically effective amount of IGF-I is administered to the individual to reduce atrophy of at least one skeletal muscle having reduced use due to a repair.

In an alternate embodiment, the mass of at least one striated skeletal muscle of an individual is enhanced by administering an effective amount of IGF-I to the individual, thereby enhancing the mass of at least one skeletal muscle. Enhancing the mass of a muscle, as defined herein, comprises reducing the loss of muscle mass from atrophy, generally maintaining muscle mass, or increasing muscle mass. In yet another embodiment, the mass of at least one skeletal muscle of an individual is enhance, wherein the striated skeletal muscle is susceptible to atrophy.

In still another embodiment, the mass of at least one striated skeletal muscle of an individual is enhanced by administering an effective amount of IGF-I to the individual while also exercising said muscle or during an exercise regimen.

A further embodiment, of the method of this invention, comprises enhancing the effect of physical therapy on an individual, wherein said physical therapy is associated with at least one skeletal muscle being susceptible to atrophy, or having atrophy. This method includes administering a therapeutic amount of IGF-I to said individual and then conducting physical therapy, associated with said skeletal muscle on said individual. Physical therapy, as defined herein, is the treatment of a disease, trauma or condition by means of exercises directed to strengthen the muscles affected by said disease, trauma or condition.

Physical therapy can be used in response to various cases of skeletal muscle atrophy, such as the lack of use of a skeletal muscle due to injury, disease, or a limitation upon the mobility of the individual, of instance, as being bedridden, at least partially paralyzed or comatose. In one embodiment, a diarthroses joint associated with the skeletal muscle has a reduced capacity to work or move. This method can enhance the effect of physical therapy for the reduced capacity joint by enhancing the mass of at least one skeletal muscle associated with said joint. The enhancement of the mass of a skeletal muscle, associated with said diarthroses joint, can improve the stability of said joint, by strengthening its muscular support structure, and/or reduce a recovery period associated with said joint.

Thus, this method can enhance the effect of physical therapy for a joint having a reduced capacity due to a disease, such as osteoarthritis, rheumatoid arthritis, bursitis, gout, rheumatic fever, tuberculosis, gonorrhea and the like. This method can also enhance the effect of physical therapy on joint having a reduced capacity due to a trauma to said joint, to a skeletal muscle associated with said joint, or to another skeletal muscle, bone, joint or tendon, wherein said trauma affects the use of said joint an/or said skeletal muscle. This method can further enhance the effect of physical therapy upon recovery from a repair of a bone, joint, muscle and/or tendon.

The dose and dose frequency for administering IGF-I, according to the method of invention, is dependent upon the size, weight, gender, of the individual being treated and the method of administration and it should be individualized. Typically the dose ranges from about 200–1,000 $\mu$g/kg/day until a clinical response such as when the muscle mass is about the same as the non-affected limb.

In the method of this invention, IGF-I, or its pharmaceutically acceptable salts, can be administered parenterally. Parenteral administration can be by transdermal or systemic application. Systemic application includes intramuscular, or subcutaneous injection. These injectable forms are prepared by known pharmacist's art.

To enhance the therapeutic spectrum, IGF-I can also be administered in conjunction with one or more therapeutic agents, such as analgesics, antibiotics, beta$_2$ agonist e.g. clenbuterol, and anti-inflammatory agents, e.g. corticosteriods, piroxicam and the like. IGF-I used herein is available from:

Cephalon, Inc., West Chester, Pa.
Chiron, Inc., Emeryville, Calif. 94601
Peptide Institute, Inc., Japan The chemistry of IGF-I is described for example in U.S. Pat. No. 5,093,317.

The invention will now be further and specifically described by the following examples.

EXAMPLE I

Comparison Test

To assess the efficacy of treatment with IGF-I on the retention of striated skeletal muscle mass, during atrophy-susceptible conditions, a test is conducted on three groups of animals regarding the effect of IGF-I treatment upon the animals with immobilized joints.

To assess the efficacy of treatment with IGF-I on the retention of striated skeletal muscle mass or reduce the time required for these muscles to return to control levels during or after atrophy-susceptible conditions such as arthritis, orthopedic surgery and periods of limb immobilization.

Adult rats, rabbits or dogs are used in these studies. Animals are maintained on standard laboratory chow and housed in USDA approved cages. Various control and treatment groups consisting of 8–10 rats or rabbits are maintained on standard laboratory chow and water ad libitum. On the other hand 4–5 dogs per group are fed standard dog chow twice per day and water is available ad libitum.

The studies consist of the following:
A. No exercise
 1. Negative control—no treatment
 2. Positive control—IGF-I
 3. Immobilization (with or without surgery)—no treatment
 4. Immobilization (with or without surgery)—IGF-I Treatment is initiated at the time of immobilization (200–1,000 $\mu$g/kg/day) subcutaneously or intramuscularly and continued for 15 weeks. One-third of the animals from each group will be killed at 5, 10, and 15 weeks. The right hind limb will be immobilized at (90° flexion) for 5 weeks with a fiberglass cast. The animals are remobilized for 10 weeks and allowed normal movement in their cages.

A second study (B) utilizing the same protocol as study (A) except following remobilization the animals are exercised 5 days per week.

The study parameters include:
1. Initial body weights and weekly body weights throughout the study.
2. Food consumption.
3. Limb circumference (e.g. thigh).
4. Clinical signs are being observed.
5. Following autopsy, muscle mass (soleus, plantaris, gastrocnemius), protein and RNA content are assessed.
6. Cross-sectional area of myofibril and myofibriller protein degradation are evaluated in the various muscle samples.
7. Organ weights (heart, liver, kidney, testis, adrenal) will be taken at autopsy.
8. Blood chemistry.

A positive response is obtained when the muscle mass in the experimental limb appropriates that of the control limb.

Those skilled in the art will recognize, or be able to ascertain, using no more than routine experimentation, many equivalents to specific embodiments of the invention described specifically herein. Such equivalents are extended to be encompassed in the scope of the following claims.

I claim:
1. A method for enhancing the effect of physical therapy on a joint of an individual, wherein said joint has reduced mobility and is associated with a skeletal muscle which provides muscular support for said reduced mobility of said joint comprising the steps of:
 a) administering a therapeutically effective amount of Insullin-Like Growth Factor-I to said individual to increase the mass of said skeletal muscle and strengthen the muscular support of said reduced mobility joint; and b) conducting physical therapy, associated with said reduced mobility of said joint, on said individual, whereby said physical therapy is enhanced by administration of Insulin-Like Growth Factor-I.

2. A method of claim 1 wherein the reduced mobility of said joint is due to an injury.

3. A method of claim 2 wherein the reduced mobility of said joint is due to a disease.

4. A method of claim 2 wherein the reduced mobility of said joint is due to at least partial immobilization of said joint.

5. A method of claim 4 wherein the reduced mobility of said joint is due to orthopedic surgery.

6. A method of claim 2 wherein the reduced mobility of said joint is due to a limitation upon the mobility of the individual.

* * * * *